United States Patent [19]

Blair et al.

[11] Patent Number: 4,650,418

[45] Date of Patent: Mar. 17, 1987

[54] DENTAL RESTORATION SHADING

[75] Inventors: John J. Blair, York; Roger C. Shue, Red Lion, both of Pa.

[73] Assignee: Dentsply Research & Development Corp., Milford, Del.

[21] Appl. No.: 724,330

[22] Filed: Apr. 17, 1985

Related U.S. Application Data

[63] Continuation-in-part of Ser. No. 576,100, Feb. 1, 1984, abandoned.

[51] Int. Cl.⁴ .............................................. A61C 13/08
[52] U.S. Cl. ................................... 433/203.1; 433/26
[58] Field of Search ................. 433/212, 208, 223, 26, 433/203, 218, 222

[56] References Cited

U.S. PATENT DOCUMENTS

| | | | |
|---|---|---|---|
| 2,302,375 | 11/1942 | Myerson | 433/203 |
| 3,449,832 | 6/1969 | Connan | 433/203 |
| 3,481,772 | 12/1969 | MacNairn et al. | 433/218 |
| 3,834,024 | 9/1974 | Kochavi | 433/207 |
| 3,839,055 | 10/1974 | Grossman | 433/203 |
| 3,934,348 | 1/1976 | Janjic | 433/222 |
| 3,986,261 | 10/1976 | Faunce | 433/203 |
| 4,115,922 | 9/1978 | Alderman | 433/26 |
| 4,207,678 | 6/1980 | Jeanette | 433/203 |
| 4,264,640 | 4/1981 | Infante | 433/203.1 |
| 4,392,829 | 7/1983 | Tanaka | 433/222 |

FOREIGN PATENT DOCUMENTS 1148306  6/1983  Canada .
0022655  1/1981  European Pat. Off. .

OTHER PUBLICATIONS

Title page, Copyright notice page, page showing Munsell Hue Value and Chroma, page showing Chroma from the McGraw-Hill Dictionary of Scientific and Technical Terms, Third Edition.
Bioform ® Shade Guide (Complete Box).
The Dentsply Technique for Biobond ® Acid Etched Resin Bonded Bridgework, 2 pages.
Article by John W. McLean, entitled Dr. John W. McLean Discusses the Pros and Cons of Today's Ceramic Materials and New Directions–pp. 443–447 from the Quintessence of Dental Technology, Jul./Aug. 1983.
The Trubyte ® Primer, a Glossary of Dental Terminology, Anatomical Landmarks and a Description of All Major Lines of Trubyte ® Tooth Products.
Cobond, Ceramic Bonding Alloy, Instructions for Casting and Soldering brochure.

Primary Examiner—Robert Peshock
Attorney, Agent, or Firm—Edward J. Hanson, Jr.

[57] ABSTRACT

A new type of dental prosthetic facing and a new method of preparation of dental prosthetic facings is disclosed. The dental prosthetic facing is provided with an outer shader layer, an intermediate at least substantially uncolored, translucent layer, and an opaque substructure color keyed with the shader layer to match a shade guide. The opaque substructure may be a metal support with a surface opaquing agent in one species.

The dental prosthetic facing may be prepared by removably mounting an intermediate uncolored translucent layer that is a crown on a color keyed opaque substructure that is a dental mount. The dental mount being matched to an opaque dental cement that will mount the finished shaded dental crown.

37 Claims, 5 Drawing Figures

DENTAL RESTORATION SHADING

This application is a continuation-in-part of application Ser. No. 06/576,100 filed Feb. 1, 1984 and is now abandoned.

BACKGROUND OF THE INVENTION

This invention relates to shaded and/or colored dental restorations or prosthesis and methods for their preparation and especially to dental restorations that appear more natural and esthetically appealing.

It has long been known in the dental profession that the good esthetics of dental prostheses are to a significant degree determined by the hue, the chroma and the value of the visibly exposed portions of the dental restoration. These qualities follow the Munsell color system for designating color which employs three perceptually uniform scales (Munsell hue, Munsell value and Munsell chroma) defined in terms of daylight reflection. (McGraw-Hill Dictionary of Scientific and Technical Terms—3rd Ed.). Translucency or the quality of transmitting and diffusing light, which gives a perception of depth is also an important parameter.

Insofar as is known, in the past it has been considered necessary in producing esthetically satisfactory artificial tooth restorations that are of the nature of facings, by which it is meant to include crowns and veneers, to build the facing's color throughout all of the light passing or translucent portions thereof. By throughout all the translucent portions it is meant the entire depth of the tooth prosthesis through which light passes to the eye of an observer. Building the color throughout the depth of the dental restoration is certainly logical from the standpoint that a natural tooth does build the color throughout its depth.

It has now been discovered, however, that what might be called an optical illusion of a natural tooth appearance can be achieved by not coloring the dental prosthesis facing throughout its entire light passing depth but instead by applying an opaquing layer of specific hue and chroma overlayed with a translucent build up layer that is substantially hue and chroma free while being translucent to light and applying a shader over this uncolored layer to provide a final esthetic effect. Not only is the appearance superior but the number of build up material variations that are required to match the unique variation in natural teeth can be reduced from about 40 to a single build up material being required to satisfy substantially all of the application requirements. No shading is required between the underlying opaquing layer and the outer shader layer.

In at least one instance on a commercial basis during the 1950's and continuing at least into the 1960's, an artificial anterior tooth 33 was constructed that is represented in FIG. 4 and had an opaque lingual area 31 that did not extend to the proximity of the incisal edge of the tooth but extended interiorly past the center portion of the tooth. The opaque area was composed of a very heavily pigmented porcelain with very strong hue and chroma to the extent of substantially complete opacity. Frontwardly of this opaque area was a layer 35 of shaded porcelain having very substantial hue and chroma but retaining substantial translucency. Forwardly of layer 35 and also upwardly toward the incisal edge of the tooth is a translucent layer 36 that is substantially hue and chroma free porcelain and also substantially clear, like water. This layer 36 opens to the incisal edge of the tooth and also overlays the shaded layer 35 at the incisal lingual portion of the tooth. The labial face of the tooth has a layer 37 of pigmented porcelain having substantially no hue, being pigmented to a substantially enamel white. To this layer 37 was added as a surface coat (not shown) various shading colors mixed with a porcelain overglaze to characterize the individual teeth to more natural appearances.

To make the tooth 33, the sequence is to make the opaque portion 31 and the portion of the layer 36 above portion 31 and rearwardly of layer 35. Also independently the layer 37 and 36, except for the portion already described in the preceeding sentence is made. Then the parts are joined through layer 35.

It is known that some of the teeth 33 of FIG. 4 were ground off from the back as shown at line 5—5 of FIG. 4 to form the veneer 40 of FIG. 5, which veneer was then adhered to a metal prosthetic support part 41 shown broken away at its base. The veneer thus had an opaque metal substrate 41, an opaque cement layer 42 applied to the front face or labial face of the metal support to become a part of the support, a shaded porcelain layer 43 having substantial hue and chroma, a substantially hue and chroma free porcelain layer 44 and a labial surface layer 45 of pigmented porcelain having substantially no hue to which was added a surface shading material (not shown) as described above.

It is an object of the present invention to provide dental restorations with superior esthetic appearance.

It is a further object of the present invention to provide an easier method of producing superior esthetic dental restorations.

It is a still further object of the present invention to provide a method of producing dental restorations that enable less expensive correction of mistakenly produced hues, chromas and values.

SUMMARY OF THE INVENTION

By an aspect of the invention a dental restoration facing is provided that has an outer shader layer; an intermediate at least substantially uncolored, translucent layer; and an opaque substructure. In one preferred specie of the invention the intermediate layer is a homogeneous single cast mica glass-ceramic crown member and the outer shader layer is a shaded dental porcelain. The outer shader layer is applied to the crown member while it is removably mounted on an opaqued dental mount matched with an opaque dental cement color keyed with the shaded dental porcelain to match a shade guide.

In another preferred specie of the invention the opaque substructure is a metal support with the surface opaquing agent and the surface opaquing agent is a dental opaque porcelain. The intermediate layer is a homogeneous single layer of dental porcelain and the outer shader layer is a shaded dental porcelain.

By other aspects of the invention are provided methods of expediently producing the dental restorations of the present invention.

DESCRIPTION OF THE PREFERRED EMBODIMENT

The present invention in its preferred embodiment is a dental prosthetic facing which may be connected directly to a natural tooth as a veneer or crown or to a dental prosthetic part. The dental prosthetic facing has an outer shader layer; an intermediate, at least substantially uncolored, translucent layer and an opaque layer and a substructure, which substrate is color keyed with the shader layer to match a shade guide. Each of the layers can be made up of a plurality of lamina or plies. An aspect of the present invention is a method of preparing a dental restoration by applying to an opaque dental substrate a translucent layer substantially free of hue and chroma and a shader layer and color keying the substrate with the shader layer to match a shade guide.

In the dental crown specie of the present invention, when positioned in a patient's mouth in conventional manner the substantially uncolored, translucent layer is not open to or directly exposed to ambient light. This is because in substance all of the exposed edges of the substantially uncolored, translucent layer are engaged with the dental cement (adhesive) in position opposed to the prepared tooth or dental prosthetic part.

As used in this patent application, shader includes shading porcelains, stains, glazes and combinations and equivalents thereof. By opaque it is meant a degree or amount of opacity that in situ substantially completely eliminates any hue, chroma or value of underlying materials from having a visible effect on the structure under ambient light. By in situ it is meant when the structure is positioned in a patient's mouth and by ambient light it is meant substantially all of the ambient light conditions encountered by people in their normal lives.

In the preferred embodiments internally, that is rearwardly or lingually, of the substantially uncolored, translucent layer there is no layer having hue except the opaque layer. This provides for the simplified structure of the present invention.

There are three primary species of the genus of the present invention. One of the species involves the preparation of metal free dental crowns and/or bridges that will be put upon natural tooth stump preparation. A second specie is the preparation of a dental restoration such as a bridge or a crown having a metal substrate. The third specie is a dental veneer that may be applied to a natural tooth or a prosthetic support part. It will be understood that the shader layer is matched with an underlying opaque dental substrate in each instance. The opaque dental substrate may be either a temporary member or a substrate that from the beginning is a permanent portion of a built-up dental restoration.

Figure 1:
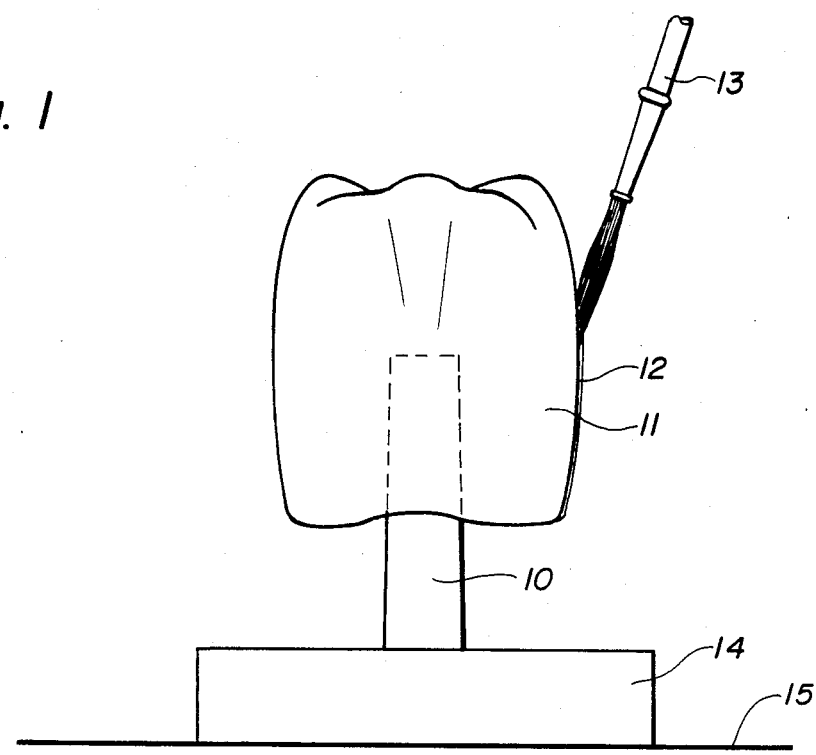
FIG. 1 is a diagrammatic view of a dental crown of the present invention positioned on a dental mount.

Considering first the procedure for preparing dental crowns and looking at FIG. 1 an opaqued dental mount 10 is shown. This opaqued dental mount may be a model of a prepared dental stump preparation made from an impression taken of a patient's mouth in the conventional manner. The dental mount may be made from an opaque material cast in the usual manner or may be cast from any suitable castable material and then provided with appropriate opaquing either by the application of a layer of opaque dental cement identical to the dental cement that will be used for subsequent mounting of the crown or another opaquing material which could be composed of a number of separate members or materials.

The opaque material should have the same hue and chroma as the dental cement that will subsequently be used in positioning the crown in a patient's mouth. It is, of course, possible to use a combination of opaquing materials and cements both on the dental mount and on the dental stump preparation in the patient's mouth so long as the combined effect is substantially the identical hue and chroma in both instances. The crown, preferably comprises of a mica glass ceramic, is prepared by known casting methods; see Canadian Pat. No. 1,148,306 to Peter J. Adair assigned to Corning Glass Works issued June 6, 1983.

Turning now to FIG. 1, the dental mount 10 can be seen. The dental mount 10 can be the die used in molding the crown or it may be one of a number of universal mounts. As a general understanding, it is not necessary that the mount be an exact fit within the crown, ie, an exact replica of the dental stump preparation in the patient's mouth. If fact, it is within the purview of the present invention for the dental mount 10 to be of a resilient or deformable material allowing a broader use within a wider range of crowns. The dental mount 10 must, however, be opaqued to the required hue and chroma as the principle is described in this patent application. It is anticipated that in usual practice the dental mount will be as nearly replica of the dental stump preparation within the patient's mouth as is commercially accepted in conventional laboratory practice at the present time and considering the use of the presently used commercial die spacers or their equivalents.

The crown 11 is preferably substantially uncolored and translucent throughout. Preferably the crown appears white and substantially free of hue and chroma to the unaided eye when viewed unmounted without internal opaque and external shader. By uncolored it will be understood to mean that there is substantially no hue. Uncolored includes white which results from light scattering or refracting due to crystaline structure or internal trapping of air and white color achieved by pigmentation. The pigmentation is useful to assure an even value for the white. The intensity of the white is its value. The crown is preferably of a material that when viewed mounted with the internal opaque dental mount passes the hue and substantially reduces the chroma of the internal opaque. In other words, the crown, or that is the body crown or main body of the crown; ie the uncolored, translucent layer should allow the hue to be seen through it while attenuating the internal chroma.

After the crown 11 has been mounted on the opaque dental mount 10, shader 12 is applied to the crown, preferably matching the crown with one of the commercial shade guides which was previously matched with the intended dental setting, typically the other teeth in a patient's mouth or the skin color and general intended esthetics that are to be provided for the patient.

The preferable shaders are of the dental porcelain type, more preferably the self glazing dental porcelains. The shader is applied to the crown using appropriate known techniques while viewing through the uncolored translucent crown to the opaque dental mount. The shader 12 is applied in conventional manner, for example with a brush 13. The shader is matched and preferably indexed to the hue, chroma and value of the opaque to complete the appearance match of the restoration to the natural tooth by the skilled dental laboratory professional.

It is clearly contemplated that the dental crown may be removed from the dental mount during staining so that the shader may be cured in several applications or layers including spotting and lining in the shader, etc., if desired. Furthermore, it is obvious that the crown itself can be made up of several layers in instances where this would be a desirable expedient.

A thus shaded and prepared crown is finally removed from the opaque dental mount and with or without further treatment to stabilize the shader layer as may be necessary, transferred to the dental operatory for placement in a patient's mouth or if it is to be applied to a supporting substrate as can be done in what is known as unit built bridgework transferred to the setting where they will be joined. In the instance where the crown will be placed upon a dental stump preparation, opaque material having substantially the same hue and chroma as the hue and chroma of the opaque dental mount is provided between the shaded crown and the substrate. For instance, when joined with a dental stump preparation dental cement is used that has been provided with opacity and the required hue and chroma.

Figure 2:
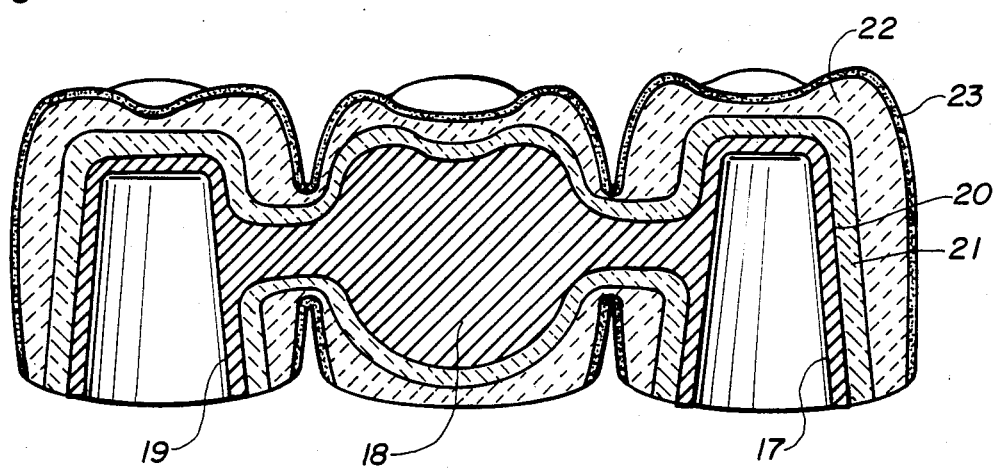
FIG. 2 is a diagrammatic sectional view of a dental bridge specie of the present invention.

Turning next to FIG. 2, a three tooth bridge is shown. The bridge is made up of the following metal substructure: a metal abutment member 17, a bridging pontic member 18 and a metal abutment member 19. The bridge is of a standard type and may be formed of either base metals or precious metals and their alloys. The upper surface metal 20 should be opaque and is shown opaqued with an opaquing layer 21. The opaquing material may be any of the known opaquing porcelain powders or their equivalents.

Of course, the opaquing may be by a multiple plied layer as well as via a singly applied homogeneous layer of material or the metal supporting base substrate could itself be formed of or coated by an appropriate opaque material having the desired hue and chroma.

Next a layer 22 of at least substantially hue free, translucent material is applied to at least a portion of the opaqued base substrate and using current accepted practice the substantially hue free or uncolored translucent material completely covers the opaque upper surfaces as shown in FIG. 2. The substantially hue free or uncolored, translucent material may be either a material such as mica ceramic glass or, more preferably, in the case of conventional metal substrates, a porcelain that is fluorescent, lightly tinted or colored and opacified to the approximate level of natural tooth enamel. The light tint would conventionally be that inherent in the natural materials from which dental porcelains are conventionally made and especially the feldspars. In special situations the natural tint could be modified with small additions of pigments to, for example, provide a uniform and consistent hue and chroma throughout a given batch of material as well as from batch to batch; which might otherwise vary due to variations in natural feldspars that are typically used to compound dental porcelains.

The substantially hue free, translucent layer 22, which can be built up or applied as a single layer to build the complete anatomical tooth form, would typically be air and/or vacuum fired in conventional manner and any necessary grinding for adjustment of the crown or bridge would then be carried out.

Finally, a shader layer 23 is applied to the translucent layer 22 remote from the opaqued base substrate surface 20. In other words, the shader is applied on the surface of the layer 22 opposite the substrate surface 20. This shader 23 provides the color match necessary to complete the dental restoration. The shader layer 23 can have incisal portions that are one shade of dental porcelain and body or neck portions that are another dental porcelain. The incisal portions may have an enamel dental portion applied to them that are very simlar in hue and chroma to the translucent layer 22.

The complete shaded dental crown or appliance can then be placed in the patient's mouth on the dental stump preparation and after testing for fit, the opaqued cement with the hue and chroma that is matched by the opaqued dental model can be interposed between the shaded dental crown and the stump preparation, typically by application of the cement to the dental stump preparation and firm seating of the crown thereover. Before the cement sets the esthetic correctness of the crown's, hue, chroma and value can be judged and if not as desired the crown can be removed and modified without destroying the crown.

Figure 3:
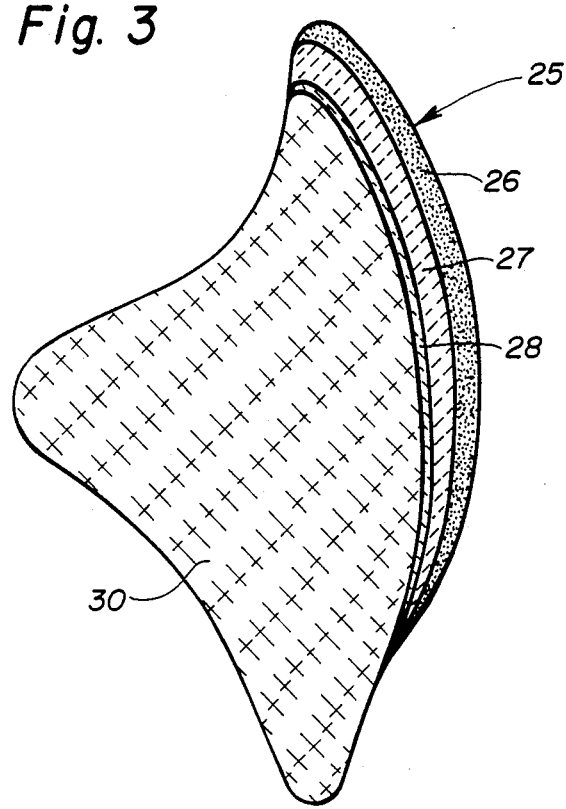
FIG. 3 is a diagrammatic sectional view of a dental veneer specie of the present invention installed on a tooth.
Figure 4:
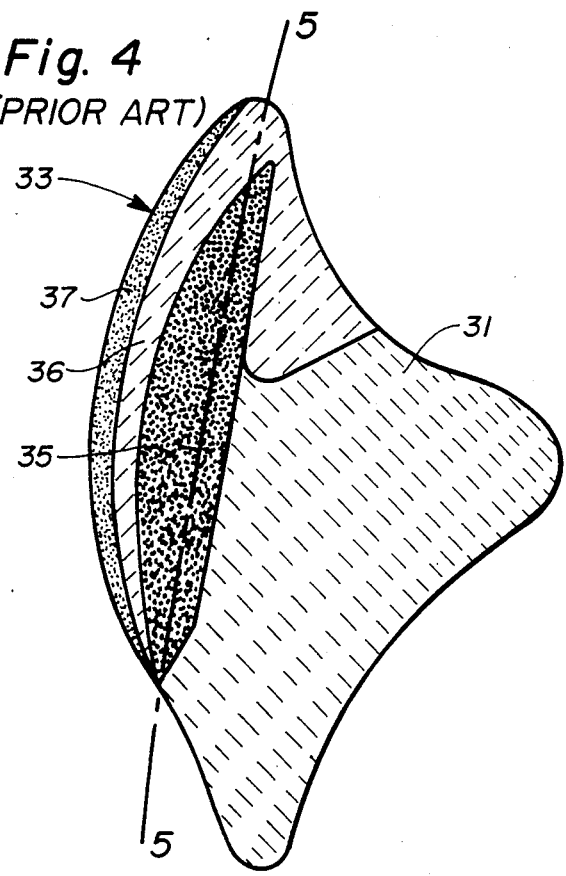
FIG. 4 is a diagrammatic sectional view of a prior art tooth.
Figure 5:
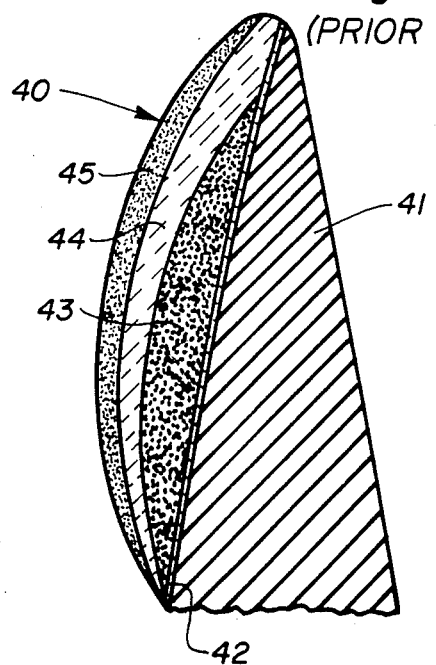
FIG. 5 is a diagrammatic sectional view of a veneer made from the tooth of FIG. 4 by sectioning at line 5—5 and securing to a metal prosthetic part which is broken away.

Turning next to FIG. 3, a dental veneer is shown mounted on a natural tooth. The veneer may be prepared from dental porcelain and with a dental cement substrate using techniques in accordance with those general techniques and procedures understood and known by dental lab personnel. The veneer 25 has an outer shader layer 26, an intermediate at least substantially uncolored translucent layer 27 and an opaque substrate cement 28 color keyed with said shader layer to match a shade guide. An uncolored translucent dental porcelain layer 27 may be formed on a model poured from an impression made of the tooth to be treated. Likewise, the layer 27 may be cast of appropriate material such as a mica glass ceramic. This uncolored translucent shell then can be mounted on an appropriately shaped dental mount that has been properly chosen for color keyed properties and the shader layer 26 applied. After this the now shaded shell can be applied to the dental cement substrate matched with the hue, chroma and value of the dental mount and thereby applied to the tooth 30 or a dental prosthetic part.

In a preferred form of the veneer, which is not the one shown in FIG. 3, the entire outwardly facing portions of the layer 27 are completely covered by the shading layer 26. Thus, no edges of the layer 27 are directly exposed to ambient light. Ambient light can, therefor, not penetrate diretcely into a surface of layer 27.

Reliance of the system of the present invention on external shade application for final color match to the patient's natural teeth, permits simple modification of the shade in the dental office or adjacent laboratory in those cases where the initial shade prescription by the dentist was in error or where the laboratory through inadvertence has failed to match a correctly prescribed shade. Modification of a complete crown through an additional application of colorants or through removal of all or part of the shaded and glazed outer surface and reapplication of the desired corrected shade and/or glaze shader can be carried out in, for example, 15 minutes or less in most instances, as contrasted to the time consuming complete rebuilding required for a conventional porcelain fused to metal restoration which relies on several layers of shaded body and enamel porcelains to achieve a desired esthetic result.

The procedure of the present invention described above results in natural esthetic color matching in far shorter times than for conventional ceramic build up techniques and reduces to one build up porcelain the 40 or more separate bottles of body and enamel porcelain powders which otherwise would be necessarily inventoried to match the wide variety of colors now offered in commercial systems in order to match the variety of shades found in natural dentition.

One of the very substantial advantages of the present procedure is that only at the stage of applying the shader is the advanced skill of the laboratory professional required in order to obtain the esthetically complimentary match intended.

Another substantial advantage of the present procedure is that modification to overcome error is much easier because the shader is only the outer layer and if the end result is not exactly satisfactory then the outer surface can be abraded with standard dental laboratory mounted stones, wheels or points or grit blasted to substantially remove the shader layer. It would also often be possible to accomplish modification through the addition of shader without necessitating any shader removal.

The invention is further illustrated by the following example:

EXAMPLE I

In an actual dental laboratory set-up the following procedure was carried out. An opaqued dental mount was prepared by taking a model of the patient's stump preparation prepared in the conventional manner and forming a cast stone die also in conventional manner.

The gypsum cast model was opaqued by thoroughly coating with a colored lacquer keyed to match the colored permanent cement that was to be used in cementing the crown to the dental stump preparation in a patient's mouth. The lacquer was Caulk® liquid opaquer—ceramic pink, (a product of the LD Caulk Division of Dentsply International, Inc.), with additional colorants added to reach a hue and chroma of a regular or standard yellow green opaquer in a thickness just great enough to totally mask the die or model.

A mica glass ceramic crown was prepared as taught in Canadian Pat. No. 1,148,306 previously referred to in this patent application using the opaqued dental mount as the die. The crown obtained an interior hollow dimension of approximately 4.5 mm (millimeters) wide and approximately 8 mm deep or penetration to receive a dental stump preparation for placement in a patient's mouth. The crown had a labial thickness of about 1.5 mm and a length of 10.0 mm.

The mica glass-ceramic crown was placed on the opaqued dental substrate as shown in FIG. 1, and shader dental porcelains were applied. The shader layer 12 was applied by using the procedures of a trained laboratory professional and matched to the BIOFORM® SHADE GUIDE—B69 using substantially standard manipulative techniques using the new staining dental porcelains described below:

The dental porcelain matrix for the body shader porcelain was prepared by tumble blending the following ingredients until visually homogeneous:

| PARTS | DESCRIPTION |
| --- | --- |
| 47.6 | Standard low thermal expansion over-glaze frit of a low viscosity glass having a particle size such |

-continued

| PARTS | DESCRIPTION |
| --- | --- |
|  | that it passed through a 270 mesh US Standard Tyler sieve and a firing to gloss temperature of 1600 to 1700° F. (Dentsply ® NBK 1000 Glaze, a product of Dentsply International, Inc.) |
| 24.83 | Yellow Brown stain (Dentsply ® stain 84) |
| 6.70 | Gray stain (Dentsply ® stain 81) |
| 9.93 | Yellow Gray stain (Dentsply ® stain 87) |
| 1.74 | Brown stain (Dentsply ® stain 86) |
| 4.47 | Red stain (Dentsply ® stain 78) |
| 3.23 | Black stain (Dentsply ® stain 82) |

The Dentsply stains are dental ceramic stains of metal oxide pigments fritted into a glass carrier.

Next, a liquid carrier medium for the glaze matrix is prepared by charging the following ingredients to a mixer in the order listed and mixing at high sheer for one minute, brushing down from the side the material that spattered up and then mixing at high sheer for another minute:

| GRAMS | DESCRIPTION |
| --- | --- |
| 3.6 | Isopropyl Alcohol (99%) |
| 90.4 | 1,3-Butanediol (99±%) |
| 6.0 | Silica (Aerosil R972, product of Degassa) |

The carrier medium and the shader matrix were then combined just prior to application by mixing in a small dish:

| QUANTITY | DESCRIPTION |
| --- | --- |
| 1 | Scoop of dry powder-Dentsply #1 scoop which holds about .8 grams |
| 5 | Drops of the liquid carrier medium |

Mixing was with a porcelain spatula to a thin paste consistency.

The first shader porcelain was applied in the usual area of the body porcelain starting at the labial side of the tooth and extending around the tooth, except not at the incisal portion for a distance of about 2 mm from the incisal edge. The staining glaze was applied to yield a thickness of less than 0.1 mm after firing.

A second glazing matrix was prepared as above except using the following recipe:

| PARTS | DESCRIPTION |
| --- | --- |
| 97.40 | Standard low thermal expansion over-glaze frit of a low viscosity glass having a particle size such that it passed through a 270 mesh US Standard Tyler sieve and a firing to gloss temperature of 1600 to 1700° F. (Dentsply ® NBK1000 Overglaze, a light orange stain product of Dentsply International Inc.) |
| 260 | Light Orange stain (Dentsply ® stain 74) |

The 2nd staining glaze was prepared in the same manner described above for the 1st staining glaze except using the second glazing matrix.

The second staining glaze is the enamel porcelain and is applied to the 2 mm wide incisal portion of the tooth and across the top of incisal edge of the tooth being shaped to form the outer incisal edge of the tooth. The enamel shader porcelain was not blended with the body shader porcelain or overlap it as is the usual practice but was simply brushed from the incisal edge to abut with the body shader porcelain or 1st staining porcelain. The thickness of application was again less than 0.1 mm yield after firing.

After application of the dental porcelain shader coat as described above, including the first body staining porcelain and the second staining glaze, the coat was dried. An oven was heated to 1450° F. and the shaded crown was inserted into the oven for 2 seconds and removed for 4 seconds and this process repeated until no additional vapor was observable; being emitted from the surface of the dental porcelain shader coat and the surface of the shader coat appeared dry. This procedure prevents blistering or the formation of bubbles. The dry shader coated crown was then fired in a sagger oven at 1450° F. to 1700° F. with a progression from 1450° F. to 1700° F. of 100° per minute.

Next, a second shader coat of the two shader porcelains was applied over the first coat in the same manner just described with regard to the first coat and dried and cured in the same manner. This is to assure complete coverage and to assure shade fidelity.

Then, the now completed stained crown with the shader layer made up of the two coats of shader, each of which is made up of a dental shader body porcelain and a dental shader enamel porcelain, was repositioned on the opaque dental mount and found to match the BIOFORM ® SHADE GUIDE—B69.

Next, a dental cement which had been pigmented to match the lacque color was applied to the dental preparation in the patient's mouth and the crown was positioned in the patient's mouth and found by visual inspection to be of excellent esthetic value. The dental cement was a zinc phosphate cement—Modern TENACIN ® SNOWITE—Caulk ®—621417 (a product of the L D Caulk Division of Dentsply International, Inc.).

EXAMPLE II

Another specie of the present invention was prepared using a supporting metal base substrate. The substrate was a three unit bridge of the general type shown in FIG. 2 except of the central, lateral and canine teeth. The bridge contained a metal abutment member or portion 17, a bridging pontic member or portion 18 and a metal abutment member or portion 19. The bridge was cast from BIOBOND ® II porcelain veneering alloy—a nickel, chromium, beryllium alloy product of Dentsply International, Inc., in conventional manner.

The upper surface 20 of the metal was opaqued with an opaquing layer 21, this opaquing material was an opaquing porcelain, (SHADEMATE TM opaque porcelain OA2, a product of Dentsply International, Inc). The opaquing porcelain was brushed on in conventional manner and fired at 1825° F. under vacuum in conventional manner to yield an opaquing layer of approximately 0.2 mm thickness.

Next, a single homogeneous layer of uncolored translucent dental porcelain (similar to SHADEMATE TM) neutral diluent was applied over the opaqued dental substrate as shown in FIG. 2 to form the intermediate or build-up layer of the final product. This layer was contoured by brush and spatula by using the procedures of a trained laboratory professional to the general anatomy of the intended teeth in the manner of FIG. 2. This intermediate layer was fired in a sagger oven at 1100° F. to 1750° F. under vacuum with a progression of 100° per minute and a hold for 1 minute at the end. A patch bake, including the addition of porcelain due to shrinkage, was carried out in the normal manner. Finally, the intermediate layer was ground and contoured. The thickness of this uncolored translucent build up layer that is to become the intermediate layer varied after firing from approximately 0.5 to 1.5 mm in thickness.

The shader was applied substantially identically to the procedure in Example I and the shader porcelains were formulated in the same manner as set forth in Example I except as follows:

The first shader porcelain matrix was prepared using the following recipe:

| PARTS | DESCRIPTION |
| --- | --- |
| 47.6 | Standard high thermal expansion over-glaze frit of a low viscosity glass having a particle size such that it passes through a 270 mesh US Standard Tyler sieve and a firing to gloss temperature of 1600 to 1700° F. (Dentsply ® Herador Glaze, a product of Dentsply International, Inc.) |
| 24.83 | Yellow Brown stain (Dentsply ® stain 84) |
| 6.70 | Gray stain (Dentsply ® stain 81) |
| 9.93 | Yellow Gray stain (Dentsply ® stain 87) |
| 1.74 | Brown stain (Dentsply ® stain 86) |
| 4.47 | Red stain (Dentsply ® stain 78) |
| 3.23 | Black stain (Dentsply ® stain 82) |

A second shader porcelain matrix was prepared as above except using the following recipe:

| PARTS | DESCRIPTION |
| --- | --- |
| 97.40 | Standard high thermal expansion over glaze frit of a low viscosity glass having a particle size such that it passes through a 270 mesh US Standard Tyler sieve and a firing to gloss temperature of 1600 to 1700° F. (Dentsply ® Herador Overglaze, a product of Dentsply International Inc.) |
| 260 | Light Orange stain (Dentsply ® stain 74) |

The finished product was inspected and found to have good esthetics.

While the invention has been primarily described with regard to the use of a shader layer that is of the typical dental porcelain that has hue and chroma and is used in preparing dental restorations it can be of other composition in special instances, for instance, a combination of dental stains over-glazed with a clear glaze could be used. It may also be desired in some instances to over-glaze the typical dental porcelains that can serve as the shader layer.

While in accordance with the patent statutes, what is considered to be the preferred embodiment of the invention has been described, it will be obvious to those skilled in the art that numerous changes and modifications may be made therein without departing from the invention and it is therefore aimed in the appended claims to cover all such equivalent variations as fall within the true spirit and scope of the invention.

It is claimed:

1. A dental prosthetic facing comprising an outer shader layer; an intermediate at least substantially uncolored translucent layer; and an opaque substrate color keyed with said shader layer to match a shade guide.

2. The dental restoration of claim 1 wherein said opaque substructure is a metal support with a surface opaquing agent.

3. The dental restoration of claim 1 wherein said intermediate uncolored translucent layer is removable mounted on said opaque substructure, said substructure comprising a dental mount.

4. The dental restoration of claim 1 wherein said substructure comprising an opaque dental cement directly engaging said intermediate uncolored translucent layer.

5. The dental restoration of claim 4 wherein said dental cement is engaged with a metal support remote from its said engagement with said intermediate uncolored translucent layer.

6. The dental restoration of claim 4 wherein said dental cement is engaged with a dental stump preparation remote from its engagement with said intermediate uncolored translucent layer.

7. The dental restoration of claim 1 wherein said intermediate layer is a homogeneous single cast mica glass-ceramic crown member, said outer shader layer comprising a shaded dental porcelain.

8. The dental restoration of claim 2 wherein said surface opaquing agent is a dental opaque porcelain, said intermediate layer is a homogeneous single layer of dental porcelain and said outer shader layer comprising a shaded dental porcelain.

9. The dental prosthetic of claim 1 constructed so that when utilized the inner at least substantially uncolored translucent layer is not directly exposed to ambient light in position in a patient.

10. A dental crown comprising an outer shader layer; and intermediate at least substantially uncolored translucent layer; and an opaque substructure.

11. The dental crown of claim 10 wherein upon positioning in a patient said intermediate uncolored translucent layer is not exposed directly to ambient light.

12. The dental crown of claim 10 wherein said opaque substructure is a metal support with a surface opaquing agent.

13. The dental crown of claim 10 wherein said intermediate uncolored translucent layer is removable mounted on said opaque substructure, said substructure comprising a dental mount.

14. The dental crown of claim 10 wherein said substructure comprising an opaque dental cement directly engaging said intermediate uncolored translucent layer.

15. The dental crown of claim 14 wherein said dental cement is engaged with a metal support remote from its said engagement with said intermediate uncolored translucent layer.

16. The dental crown of claim 14 wherein said dental cement is engaged with a dental stump preparation remote from its engagement with said intermediate uncolored translucent layer.

17. The dental crown of claim 10 wherein said intermediate layer is a homogeneous single cast mica glass-ceramic crown member, said outer shader layer comprising a shaded dental porcelain.

18. The dental crown of claim 17 wherein said substructure comprising an opaque dental cement color keyed with said shaded dental porcelain to match a shade guide.

19. The dental crown of claim 13 wherein said surface opaquing agent is a dental opaque porcelain, said intermediate layer is a homogeneous single layer of dental porcelain and said outer shader layer comprising a shaded dental porcelain.

20. A method of preparing a dental restoration comprising applying to an opaque dental substrate a translucent layer that is at least substantially free of hue and chroma, and thereafter applying a shader layer.

21. The method of claim 20 wherein said opaque dental substrate comprising opaque cement having hue and substantial chroma.

22. The method of claim 20 wherein said translucent layer appears white and substantially free of hue and chroma to the unaided eye when viewed unmounted without internal opaque and without shader and when viewed mounted with internal opaque passes the opaque's hue and substantially reduces the chroma of the internal opaque.

23. The method of preparing a dental restoration of claim 20 wherein said opaque dental substrate is a metal support with an opaque dental cement thereon directly engaging said translucent layer.

24. The method of preparing a dental restoration of claim 20 wherein said opaque dental substrate is a metal support unit with a dental opaque porcelain thereon, said translucent layer is a homogeneous single layer of dental porcelain and said shader layer comprising shaded dental porcelain.

25. The method of preparing a dental restoration of claim 20 wherein said translucent layer is removable mounted on said opaque dental substrate, said substrate comprising a dental mount having substantial hue and chroma and said method comprising removing said translucent layer from said dental mount and engaging said translucent layer with a dental cement and thereby a dental stump preparation, said dental cement being matched with the hue and chroma of said opaque dental substrate.

26. The method of preparing a dental restoration of claim 25 wherein while said translucent layer is on said dental mount, said translucent layer is treated to form said shader layer.

27. The method of preparing a dental restoration of claim 26 wherein said shaded translucent layer is at least substantially uncolored and translucent throughout except for said shader layer when removed from said opaque dental mount.

28. The method of claim 27 wherein said translucent layer appears white and substantially free of hue and chroma to the unaided eye when viewed unmounted without internal opaque and without shader and when viewed mounted with internal opaque passes the hue and substantially reduces the chroma of the internal opaque.

29. The method of preparing a dental restoration of claim 20 wherein said translucent layer has a low hue and chroma.

30. The method of preparing a dental restoration comprising preparing an opaque dental mount; placing a crown on said dental mount, said crown being at least substantially uncolored and translucent throughout; applying shader to said crown and viewing said opaque dental mount while applying said shader; and removing said shaded crown from said opaque dental mount.

31. The method of claim 30 wherein said shader is applied as outer layer to said crown and said shaded crown is at least substantially uncolored and translucent throughout except for said outer layer of shader when removed from said opaque dental mount.

32. The method of claim 31 wherein said opaque dental mount has hue and substantial chroma and comprising mounting said shaded crown on a prepared tooth stump comprising applying opaque cement having substantially the same hue and chroma as said opaque dental mount between said shaded crown and said prepared tooth stump.

33. The method of claim 32 wherein said crown appears white and substantially free of hue and chroma to the unaided eye when viewed unmounted without internal opaque and without shader and when viewed mounted with internal opaque passes the hue and substantially reduces the chroma of the internal opaque.

34. The method of claim 32 wherein said dental mount is a master model of said prepared tooth stump.

35. The method of claim 30 wherein said crown comprising mica glass-ceramic.

36. The method of claim 31 wherein said opaque dental mount has hue and substantial chroma and comprising mounting said shaded crown on a metal base member comprising applying opaque material having substantially the same hue and chroma as said opaque dental mount between said shaded crown and said metal base member.

37. The method of preparing a dental restoration comprising in sequence, first preparing a supporting base substrate, next opaquing at least a portion of said base substrate, then applying a layer of at least substantially hue free, translucent material to at least a portion of said opaqued base substrate, thereafter applying a shader to said translucent material remote from said opaqued base substrate.

* * * * *

REEXAMINATION CERTIFICATE (1178th)
United States Patent [19]
Blair et al.

[11] B1 4,650,418
[45] Certificate Issued Dec. 19, 1989

[54] DENTAL RESTORATION SHADING

[75] Inventors: John J. Blair, York; Roger C. Shue, Red Lion, both of Pa.

[73] Assignee: Dentsply Research & Development Corp., Milford, Del.

Reexamination Request:
No. 90/001,567, Jul. 25, 1988

Reexamination Certificate for:
Patent No.: 4,650,418
Issued: Mar. 17, 1987
Appl. No.: 724,330
Filed: Apr. 17, 1985

Related U.S. Application Data

[63] Continuation-in-part of Ser. No. 576,100, Feb. 1, 1984, abandoned.

[51] Int. Cl.$^4$ .............................................. A61C 13/08
[52] U.S. Cl. .................................................. 433/203.1
[58] Field of Search .................. 433/212, 208, 223, 26, 433/203, 218, 222

[56] References Cited

U.S. PATENT DOCUMENTS 4,115,922  9/1978  Alderman ............................. 433/26
4,207,678  6/1980  Jeanette ............................. 433/203.1
4,431,420  2/1984  Adair ................................. 433/199.1

OTHER PUBLICATIONS

The Dentsply "BIOBOND" Technique Manual (1982).
Dentsply "BIOBOND" Porcelain with SHADE-MATE Opaques (1983).
Adair et al. "Preliminary Clinical Evaluation of Cast Ceramic Full Crown Restorations" IADR Abst. No. 1024 (1982).
McLean, The Science and Art of Dental Ceramics, vol. I (1979) (Monographs I and III).
McLean, The Science and Art of Dental Ceramics, vol. 2 (1979) (Selected excerpts pp. 64–78; 246–247).

Primary Examiner—R. Peshock

[57] ABSTRACT

A new type of dental prosthetic facing and a new method of preparation of dental prosthetic facings is disclosed. The dental prosthetic facing is provided with an outer shader layer, an intermediate at least substantially uncolored, translucent layer, and an opaque substructure color keyed with the shader layer to match a shade guide. The opaque substructure may be a metal support with a surface opaquing agent in one species. The dental prosthetic facing may be prepared by removably mounting an intermediate uncolored translucent layer that is a crown on a color keyed opaque substructure that is a dental mount. The dental mount being matched to an opaque dental cement that will mount the finished shaded dental crown.

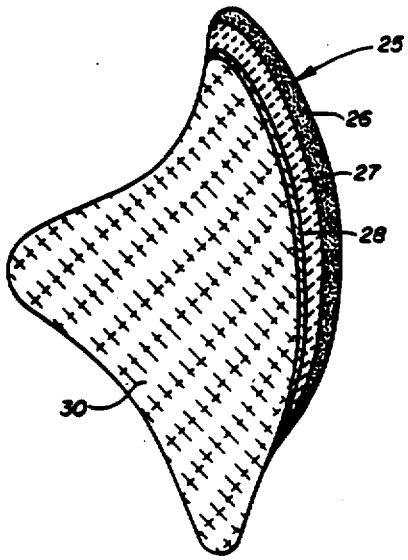

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

Claims 2–4, 7, 10, 12–14, 17, 19–21, 23–25, 30–32, 36, and 37 are determined to be patentable as amended.

Claims 5, 6, 8, 9, 11, 15, 16, 18, 22, 26–29, and 33–35, dependent on an amended claim, are determined to be patentable.

2. The dental restoration of claim 1 wherein said opaque substructure is a metal support *coated* with a surface opaquing agent.

3. The dental restoration of claim 1 wherein said intermediate uncolored and translucent layer is [removable] *removably* mounted on said opaque substructure, said substructure comprising a dental mount.

4. The dental restoration of claim 1 wherein said substructure [comprising] *comprises* an opaque dental cement directly engaging said intermediate uncolored translucent layer.

7. The dental restoration of claim 1 wherein said intermediate layer is a homogeneous single cast mica glass-ceramic crown member, *and* said outer shader layer comprising a shaded dental porcelain.

10. A dental crown comprising an outer shader layer; and intermediate at least substantially uncolored translucent layer and an opaque substructure *which has been color keyed to match a shade guide.*

12. The dental crown of claim 10 wherein said opaque substructure is a metal support *coated* with a surface opaquing agent.

13. The dental crown of claim 10 wherein said intermediate uncolored *and* translucent layer is [removable] *removably* mounted on said opaque substructure, said substructure comprising a dental mount.

14. The dental crown of claim 10 wherein said substructure [comprising] *comprises* an opaque dental cement directly engaging said intermediate uncolored translucent layer.

17. The dental crown of claim 10 wherein said intermediate layer is a homogeneous single cast mica glass-ceramic crown member, *and* said outer shader layer comprising a shaded dental porcelain.

19. The dental crown of claim [13] *12* wherein said surface opaquing agent is a dental opaque porcelain, said intermediate layer is a homogeneous single layer of dental porcelain and said outer shader layer comprising a shaded dental porcelain.

20. A method of preparing a dental restoration comprising *the steps of:*

[applying to] (a) *preparing* an opaque dental substrate *by applying an opaque material which has been color keyed to a shade guide to a support*

(b) *applying* a translucent layer that is at least substantially free of hue and chroma *to said opaque dental substrate,* and

[thereafter] (c) applying a shader layer *to said translucent layer.*

21. The method of claim 20 wherein said opaque dental substrate comprising opaque *dental* cement having hue and substantial chroma.

23. The method of preparing a dental restoration of claim 20 wherein said opaque dental substrate is a metal support *coated* with an opaque dental cement thereon directly engaging said translucent layer.

24. The method of preparing a dental restoration of claim 20 wherein said opaque dental substrate is a metal support unit with a dental opaque porcelain thereon, *and* said translucent layer is a homogeneous single layer of dental porcelain and said shader layer comprising shaded dental procelain.

25. The method of preparing a dental restoration of claim 20 wherein said translucent layer is [removable] *removably* mounted on said opaque dental substrate, said substrate comprising a dental mount having substantial hue and chroma and said method comprising removing said translucent layer from said dental mount and engaging said translucent layer with a dental cement and thereby a dental stump preparation, said dental cement being matched with the hue and chroma of said opaque dental substrate.

30. The method of preparing a dental restoration comprising *the steps of:*
(a) preparing an opaque dental mount *by applying an opaque material which has been color keyed to a shade guide to a support;*
(b) placing a crown on said dental mount, said crown being at least substantially uncolored and translucent throughout;
(c) applying shader to said crown and viewing said opaque dental mount while applying said shader *to produce a shaded crown;*
(d) and removing said shaded crown from said opaque dental mount.

31. The method of claim 30 wherein said shader is applied [as] *to the* outer [layer to] *surface of* said crown *to produce a shaded crown* and said shaded crown is at least substantially uncolored and translucent throughout except for said outer layer of shader when removed from said opaque dental mount.

32. The method of claim 31 wherein said opaque dental mount has hue and substantial chroma, [and] *said method* comprising mounting said shaded crown on a prepared tooth stump [comprising] *wherein said tooth stump is prepared by* applying opaque cement having substantially the same hue and chroma as said opaque dental mount between said shaded crown and said prepared tooth stump.

36. The method of claim 31 wherein said opaque dental mount has hue and substantial chroma [and] *said method* comprising mounting said shaded crown on a metal base member [comprising] *by* applying opaque material having substantially the same hue and chroma as said opaque dental mount between said shaded crown and said metal base member.

37. The method of preparing a dental restoration comprising in sequence,
[first] (a) preparing a supporting base substrate,
[next] (b) opaquing at least a portion of said base substrate *wherein the opaque used is color keyed to a shade guide,*
[then] (c) applying a layer of at least substantially hue free, translucent material to at least a portion of said opaqued base substrate, *and*
[thereafter] (d) applying a shader to said translucent material remote from said opaqued base substrate.

* * * * *